United States Patent [19]

Heppke et al.

[11] Patent Number: 4,997,591
[45] Date of Patent: Mar. 5, 1991

[54] CHIRAL SMETIC LIQUID CRYSTALS AND GLASSY MATERIALS CONTAINING THE SAME FOR DISPLAYING AND STORING INFORMATION

[75] Inventors: Gerd Heppke; Feodor Oestreicher, both of Berlin, Fed. Rep. of Germany

[73] Assignee: Hoechst Aktiengesellschaft, Frankfurt am Main, Fed. Rep. of Germany

[21] Appl. No.: 392,712

[22] Filed: Aug. 11, 1989

[30] Foreign Application Priority Data

Aug. 13, 1988 [DE] Fed. Rep. of Germany ....... 3827603

[51] Int. Cl.$^5$ ............................................ C09K 19/34
[52] U.S. Cl. ........................... 252/299.61; 252/299.63; 252/299.66; 252/299.67; 252/299.65; 252/299.01; 544/298; 560/62; 560/64; 560/102; 560/54; 528/25; 568/20; 568/24; 350/350 S
[58] Field of Search ............... 350/350 S; 252/299.61, 252/299.63, 299.65, 299.66, 299.67, 299.01, 299.61; 544/298, 54; 560/62, 64, 102; 568/20, 24; 528/25

[56] References Cited

U.S. PATENT DOCUMENTS

| | | |
|---|---|---|
| 4,774,028 | 9/1988 | Imai et al. .................. 252/299.01 X |
| 4,876,028 | 10/1989 | Hemmerling et al. ......... 252/299.61 |
| 4,892,675 | 1/1990 | Nohira et al. ................. 252/299.01 |
| 4,923,633 | 5/1990 | Gray et al. .................... 252/299.65 |

Primary Examiner—Robert L. Stoll
Assistant Examiner—C. Harns
Attorney, Agent, or Firm—Curtis, Morris & Safford

[57] ABSTRACT

The chiral smetic liquid-crystalline compounds of the general formula (I)

$$M_1{}^*-B-M_2{}^* \qquad (I)$$

solidify on cooling from the liquid-crystalline phase in glassy form, as a result of which they are suitable for materials for displaying and storing information. Such materials may be used in electro-optic data stores or display components which are based on the ferroelectric or electroclinic switching effect in a chiral or chirally doped, smetic liquid-crystalline phase.

In the general formula, $M_1{}^*$, $M_2{}^*$ stand for chiral smetogenic groups and —B— is, as bridging link, a typical bivalent group.

4 Claims, No Drawings

CHIRAL SMETIC LIQUID CRYSTALS AND GLASSY MATERIALS CONTAINING THE SAME FOR DISPLAYING AND STORING INFORMATION

The unusual combination of anisotropic and fluid properties of liquid crystals has resulted in their use in a multiplicity of electro-optic switching and displaying devices. In these, use may be made of their electrical, magnetic, elastic and/or thermal properties for the purpose of changes in orientation. Optical effects can then be achieved with the aid of their double refraction ("birefringence mode"), the incorporation of dichroically absorbing dyestuff molecules ("guest-host mode") or of light scattering. For this purpose, nematic liquid-crystal phases have hitherto preferably been used, but also in addition smectic liquid-crystal phases, in particular the chiral smectic-C phase ($S_C^*$) and the smectic-A phase ($S_A$).

The $S_A$ and $S_C$ phases have a layer structure with randomly distributed molecular centers of mass within a layer. They differ in that, in the $S_A$ phase, the director n is perpendicular to the layer plane, i.e. parallel to the layer normal Z (definition of the orthogonal phases), but in the $S_C$ phase there is a tilt which is specified by the angle $\Theta$ between n and z (definition of the inclined phases or "tilted phases").

According to Clark and Lagerwall [N.A. Clark and S.T. Lagerwall, Appl. Phys. Lett. 36, 899 (1980)], the ferroelectricity of the $S_C^*$ phase may be exploited to produce an electro-optic effect. This is based on the existence of two stable states between which a rapid switching takes place in typically 50 $\mu$s for an electric field of 10; V/m [R.B. Meyer et al., J. Phys. (Paris) Letters 36, L-69 (1975)]. This ferroelectric effect is notable for an extremely nonlinear electro-optic characteristic curve. It is known that, in the $S_A^*$ phase (chiral $S_A$ phase), a related, but nonlinear, process occurs which according to Garoff and Meyer [S. Garoff et al., Phys. Rev. Lett. 38, 848 (1977)] is called the electroclinic effect. It is due to a field-induced tilt angle $\Theta$, which is proportional to the electric field E extending parallel to the smectic layers, in the per se orthogonal $S_A^*$ phase. Recently it was found that this effect also occurs in more highly ordered orthogonal smectic phases such as $S_B$ and $S_E$ [C. Bahr et al., Physical Review A, 37, 3179 (1988)].

Owing to the linearity of the electroclinic effect, the preferred direction of the long molecular axes and, consequently, the main axis of the indicatrix can be continuously rotated by applying an electric field and in particular, depending on the field direction, in the clockwise or counterclockwise direction.

Between two polarizers which are preferably in the crossed position, the light intensity therefore also varies continuously and as the electric field is continuously increased, passes through a continuous gray scale, for example from black through ever lighter gray to white.

The (nonlinear) ferroelectric effect in the $S_C^*$ phase and the (linear) electroclinic effect in the $S_A^*$ phase are all the more marked, i.e. can be carried out with small voltages, the greater the spontaneous polarization in the $S^*$ phase is.

Typical chiral compounds which induce a high spontaneous polarization are the mesogenic $\alpha$-halocarboxylic acid derivatives or oxirane ester derivatives known from the prior art.

In order to store information written-in with the aid of an electric field, it is necessary for the $S_C^*$ or $S_A^*$ liquid-crystalline phase not to crystallize out since said information would vanish in the crystallization process but, instead of, to form a glass or a state comparable therewith during cooling.

Such behavior is known, for example, from the cooling of polymeric liquid crystals (see, for example, H.) Finkleman in "Polymer Liquid Crystals", edited by A. Cigerri, W.R. Krigbaum and R.B. Meyer, Academic Press 1982) but in low-molecular ("monomeric") liquid crystals, a "glass" formation is almost never observed. On the other hand, these "monomeric" liquid crystals in particular can, however, be very rapidly switched, but the polymeric liquid crystals, on the other hand, only very slowly.

The object of the present invention is therefore to find liquid crystals or liquid crystal mixtures which are both capable of being rapidly switched and which also would be able to store information written-in by such switching operations.

This object is achieved by chiral smectic liquid-crystalline compounds of the general formula (I)

$$M^*_1 - B - M^*_2 \qquad (I)$$

in which $M^*_1$, $M^*_2$ are, independently of each other, but in particular, identical chiral smectogenic groups and the bridging link —B— stands for a bivalent group, and which simultaneously solidify in a glassy form from the liquid-crystalline phase on cooling. The object set is further achieved by glassy materials for displaying and storing information which contain such compounds of the general formula (I) or are composed thereof.

The term "smectogenic groups" is understood to mean those groups which promote the development of smectic phases or produce them. The said compounds of the general formula (I) combine within them the property of a rapid ferroelectric or electroclinic switching and the ability to store the "written-in" information by glassy solidification of the liquid-crystalline phase. The compounds are often also described below as dimers. Dimers forming glassy phases are described for nematic liquid crystals in a number of publications (Demus et al., in DD-A 242,624, 242,625, 242,626, 242,627 or 247,227). These nematic dimers can be produced by bridging two nematogenic molecular groups, i.e. molecular groups promoting the development of a nematic phase.

The use according to the invention of the chiral smectic dimers which solidify in glassy form results in an optical display and storage component which is constructed in principle like a normal liquid crystal display (see, for example, B. Bahadur, Mol. Cryst. Liq. Cryst. 109 (1), 1984 or E. Kaneko, "Liquid Crystal TV Displays: Principles and Applications of Liquid Crystal Displays", KTK Scientific Publishers, 1987), that is to say, contains glass support plates, transparent electrodes, orientation layers, possibly a color filter matrix, alignment and passivation layers, polarization foils etc. As an additional component, however, a device is required for short-term heating which operates either punctiformly (such as, for example, as a result of an alignable laser) or over the entire area of the cell. In the heated state, a chiral smectic liquid-crystalline phase containing the compounds according to the invention or composed thereof can be switched very rapidly; on cooling, this switching state obtained is frozen in as a glass (in glassy form) and therefore remains stored. In this way, it is possible to write, correct (i.e. overwrite) or erase punctiformly or as an image. The information may be read, for example, on the basis of the optical transmission.

In addition to the very much shorter addressing times of the chiral smectic crystals (200 ns to 200 μs) compared with nematic or polymeric liquid-crystalline phases (greater than 10 ms), the particular advantages of using chiral smectic phases is the possibility of pulsed addressing of $S_C^*$ phases or the possibility of being able to store a continuous gray scale in the case of the $S_A^*$ phases. In addition, the reorientation in chiral smectic phases depends on the electric field direction, which increases the available information density compared with the nematic techniques which exploit the dielectric reorientation.

The compounds according to the invention $$M^*_1-B-M^*_2 \qquad (I)$$

result, for example, from the following combinations of groupings:

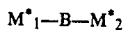

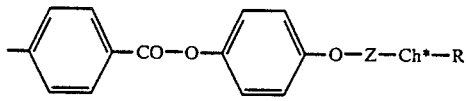

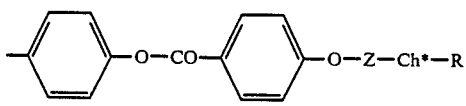

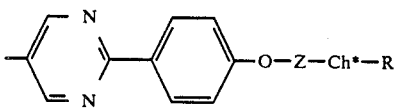

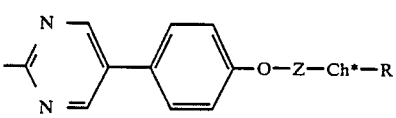

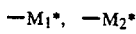

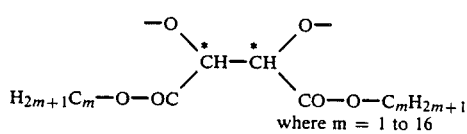

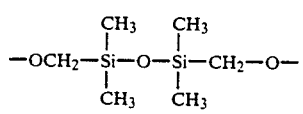

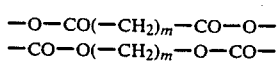

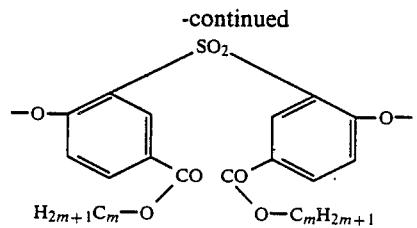

where

R denotes a straight-chain or branched alkyl radical from $C_1$ to $C_{16}$ or an alkenyl radical from $C_2$ to $C_{16}$ which may also be substituted by F, Cl and/or CN, or in which 1 or 2 nonadjacent carbon atoms (from carbon atom 2 after the $CH^*$) may also be replaced by —O—, —S—, —O—CO—, —CO—O—, —S—CO— or —CO—S—, —Ch*— denotes a bivalent chiral group which effects a high spontaneous polarization in the molecule, such as —CHCl—, —CHF— or

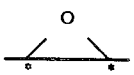

and —Z— denotes —CO— or $(-CH_2)_n$—, where n = 1 to 8.

Compounds of this type can be prepared by synthesis known from the literature from commercially obtainable substances, as the reaction routes (a) and (b) below show by way of example.

The smectogenic radical $M^*_1$ or $M^*_2$ should advantageously be chosen in a manner such that the spontaneous polarization or the electroclinic coefficient is as high as possible. This is achieved by using chiral groups of the type specified above.

Reaction Route (a)

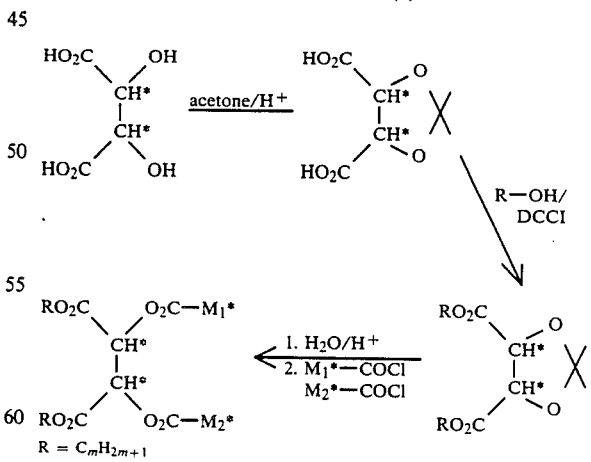

The two free hydroxyl groups of the tartaric acid molecule are first protected as acetonides by ketalization and then the acid functions are esterified. After detaching the protective function and esterifying the hydroxyl groups, the desired compounds are obtained.

Reaction Route (b)

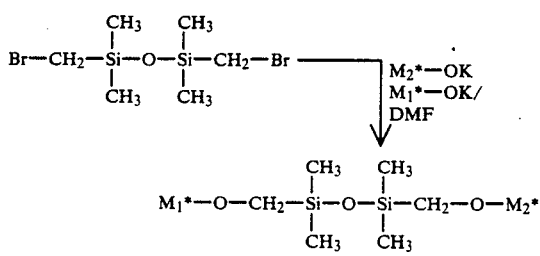

Available for the preparation of the compounds containing bis(oxymethyl)tetramethyldisiloxane as bridging link are the corresponding bis(bromomethyl)disiloxyl compounds which are known from the literature and which are reacted with mesogenic potassium phenolates in a Williamson ether synthesis.

We claim:

1. A chiral smectic liquid-crystalline compound of the general formula (I)

$$M^*_1—B—M^*_2 \qquad (I)$$

in which $M^*_1$, $M^*_2$ are, independently of each other, but in particular, identical chiral smectogenic groups and the bridging link —B— stands for a bivalent group, and which simultaneously solidify in a glassy form from the liquid-crystalline phase on cooling.

2. A glassy material for displaying and storing information which contains such compounds of the general formula (I) as claimed in claim 1 or is composed thereof.

3. An electro-optic data store or electro-optic display component based on the ferroelectric or electroclinic switching effect in a chiral or chirally doped, smectic liquid-crystalline phase having a content of compounds of the general formula (I) as claimed in claim 1.

4. A compound as claimed in claim 1 having the following meaning of the symbols:

$—M_1^*, \ —M_2^*$

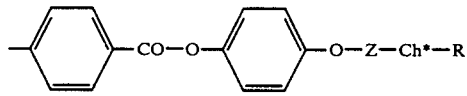

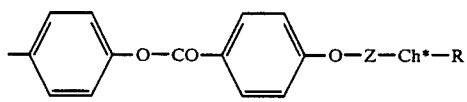

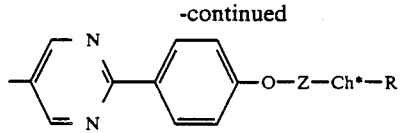

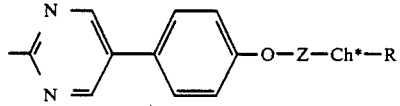

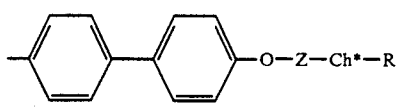

—B—

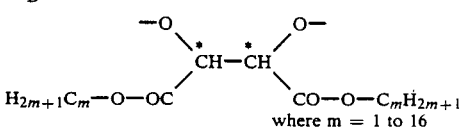

where m = 1 to 16

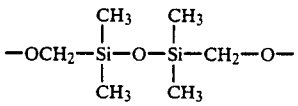

—O—CO(—CH$_2$)$_m$—CO—O—
—CO—O(—CH$_2$)$_m$—O—CO—

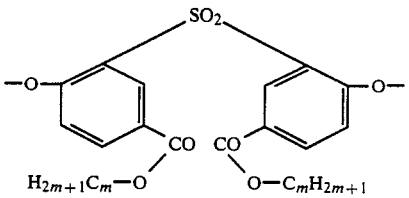

where
R denotes a straight-chain or branched alkyl radical from $C_1$ to $C_{16}$ or an alkenyl radical from $C_2$ to $C_{16}$ which may also be substituted by F, Cl and/or CN, or in which 1 or 2 nonadjacent carbon atoms (from carbon atom 2 after the CH*) may also be replaced by —O—, —S—, —O—CO—, —CO—O—, —S—CO— or —CO—S—,
—Ch*— denotes a bivalent chiral group which effects a high spontaneous polarization in the molecule, such as —CHCl—, —CHF— or

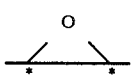

and
—Z— denotes —CO— or (—CH$_2$)$_n$—, where n=1 to 8.